(12) United States Patent
Aiello et al.

(10) Patent No.: US 6,284,751 B1
(45) Date of Patent: Sep. 4, 2001

(54) THERAPEUTIC TREATMENT FOR VEGF RELATED DISEASES

(75) Inventors: Lloyd P. Aiello, Belmont, MA (US); Michael R. Jirousek, Indianapolis, IN (US); George L. King, Dover, MA (US); Louis Vignati; Douglas Kirk Ways, both of Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 09/335,887

(22) Filed: Jun. 18, 1999

Related U.S. Application Data

(62) Division of application No. 08/841,635, filed on Apr. 30, 1997.
(60) Provisional application No. 60/016,658, filed on May 1, 1996.

(51) Int. Cl.⁷ .................. A61K 31/33; A61K 31/555; A61K 31/40
(52) U.S. Cl. .................. 514/183; 514/184; 514/185; 514/410
(58) Field of Search .................. 514/183, 184, 514/185, 410

(56) References Cited

U.S. PATENT DOCUMENTS

| | | | |
|---|---|---|---|
| 5,057,614 | 10/1991 | Davis et al. | 548/466 |
| 5,481,003 | 1/1996 | Gillig et al. | 548/455 |
| 5,491,242 | 2/1996 | Gillig et al. | 548/455 |
| 5,516,771 | 5/1996 | Dionne et al. | 514/410 |
| 5,545,636 | 8/1996 | Heath, Jr. et al. | 514/214 |
| 5,552,396 | 9/1996 | Heath, Jr. et al. | 514/183 |
| 5,621,098 | 4/1997 | Heath, Jr. et al. | 540/472 |
| 5,624,949 | 4/1997 | McDonald et al. | 514/410 |
| 5,780,461 | 7/1998 | Heath, Jr. et al. | 514/183 |

FOREIGN PATENT DOCUMENTS

| | | |
|---|---|---|
| 0 657 411 A1 | 2/1994 | (EP) . |
| 0 657 458 | 6/1995 | (EP) . |

OTHER PUBLICATIONS

Akinaga et al. "Diverse Effects of Indolocarbazole Compounds on the Cell Cycle Progression of ras–transformed Rat Fibroblast Cell" J. Antibiot., vol. 46, No. 1, 1993 pp. 1767–1771.
Akinaga et al. "Antitumor effect of KT6124, a novel derivative of protein kinase inhibitor K–252a, and its mechanism of action" Cancer Chemother. Pharmacol., vol. 29, No. 4, 1992, pp. 266–272.
Bundgaard, H. *Design of Prodrugs*, (1985).
Claffey, et al., Cancer Research 56, 172–181 (1996).
Denekamp J. *Br J Radiol 66*: 181–196, 1993.
Flier et al., *The New England Journal of Medicine*, vol. 333 pp1757–1763, 1995.
Folkman, J. Tumor angiogenesis In Mendelsohn J. Howley PM, Israel MA. Liotta LA. eds. The Molecular Basis of Cancer, Philadephia: W.B. Saunder, 1995:206–232.
Muthukrishnan, et al., *J. Cell Physiol.*, 148:1–16 (1991).
Pepper, et al., *Biochem Biophys Res. Commun.*, 189:824–831 (1992).
Jacobson et al., "Anti–inflammatory Properties of Go 6850: A Selective Inhibitor of Protein Kinase C," J. Pharm. Expl. Ther., vol. 275, No. 2, pp. 995–1002 (1995).

*Primary Examiner*—Jerome D. Goldberg
(74) *Attorney, Agent, or Firm*—Paul R. Darkes

(57) ABSTRACT

A method for inhibiting VEGF stimulated endothelial cell growth, such as associated with neoplasia, and VEGF stimulated capillary permeability, such as associated with pulmonary edema are disclosed, particularly using the β-isozyme selective PKC inhibitor, (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dionehydrochloridesalt.

4 Claims, 4 Drawing Sheets

THERAPEUTIC TREATMENT FOR VEGF RELATED DISEASES

This application claims the priority benefit of the U.S. Provision, cation Ser. No. 60/016,658 filed May 1, 1996. This application is a divisional of U.S. Ser. No. 08/841,635, filed Apr. 30, 1997, pending.

BACKGROUND OF THE INVENTION

1. Field of the Invention

The present invention is broadly directed to a method for inhibiting endothelial cell growth and capillary permeability associated with vascular endothelial growth factor (VEGF), e.g., the increased cell growth and permeability induced by (VEGF) using an inhibitor of the β isozyme of Protein Kinase C (PKC). This VEGF induced condition is closely associated with neoplasia in mammals and other disorders including pulmonary edema.

The present invention is particularly directed to the use of an inhibitor of the β isozyme of Protein Kinase C (PKC) for treating neoplastic diseases including capillary hemangioblastomia, breast cancer, Kaposi's sarcoma, glioblastoma, angiomatous disorders, colorectal cancer, medulloblastoma, gastric carcinoma, adenocarcinomas of the gastrointerestinal tract, malignant melanoma, ovarian cancer, non small cell lung cancer, prostate cancer, malignant effusions, preitumoral edema, e.g., intracerebral edema and cysts associated with brain tumor, bladder carcinoma, von Hippel Lindau Syndrome, renal cell carcinoma, skin cancer, thyroid malignancies, cervical cancer, hepatocellular carcinoma, rhabdomyosarcoma, and leiomysarcoma and certain other VEGF related disorders as described herein.

2. Description of Related Art

VPF/VEGF is a glycosylated, multifunctional cytokine. Over-expression of VPF/VEGF is associated with neoplasia, and several other disease conditions.

VPF/VEGF induces endothelial cell proliferation, excessive permeability via activation of vesicular-vacuolar organelle mediated transport, migration and actin reorganization with shape changes and ruffling. It alters endothelial cell gene expression, inducing increased production of tissue factor and several proteases, including interstitial collagenase and both the urokinase-like and tissue plasminogen activators. The majority of these same genes are induced by phorbol myristate acetate (PMA) stimulated activation of PKC.

VPF/VEGF is abundantly expressed and secreted by most human and animal tumors examined thus far. VPF/VEGF may directly affect tumor cells, e.g., tumor cells of glioblastoma, as well as play an important role in the induction of tumor angiogenesis (Claffey, et al., Cancer Research 56, 172–181 (1996) and the references cited therein).

The angiogenic potential of VEGF likely is enhanced by the synergistic activity of fibroblast growth factor liberated by cellular disruption or death. (Pepper, et al., *Biochem Biophys Res. Commun.*, 189:824–831 (1992); Muthukrishnan, et al., *J. Cell Physiol.*, 148:1–16 (1991)).

Tumor growth and metastasis are closely related to enhanced VEGF expression. A chemical signal from tumor cells can shift resting endothelial cells into a phase of rapid growth. Of the twelve known angiogenic proteins, those most commonly found in tumors appear to be basic fibroblast growth factor (bFGF) and vascular endothelial growth factor (VEGF), also known as vascular permeability factor (VPF) (Folkman, *J. New England J. of Medicine.*, Vol 999 (26): 1757–1763(1995) and the references cited therein).

The realization that tumor growth requires new blood vessels and the identification of chemical factors that mediate neovascularization or angiogenesis have broadened the understanding of pathologic processes and opened new avenues to the treatment of these diseases. Nine different inhibitors of angiogenesis are currently being studied in phase 1 or 2 clinical trials as treatment for a wide spectrum of solid tumors, including breast, colon, lung, and prostate cancer as well as Kaposi's sarcoma. (Folkman, J. Tumor angiogenesis In Mendelsohn J. Howley P M, Israel M A. Liotta L A. eds. The Molecular Basis of Cancer, Philadelphia: W. B. Saunders. 1995:206–232) One of these drugs, TNP-170, a synthetic analogue of fumagillin (Denekamp *J. Br J Radiol* 66:181–196,1993) has been approved by the FDA for phase 1 testing in many patients with solid tumors. Other inhibitors of angiogenesis currently in clinical trials in patients with advanced cancer include platelet factor 4; carboxyaminotriazole; BB-94 and BB-2516; metalloproteinase inhibitors; the sulfated polysaccharide tecogalan (DS-152); thalidomide; interleukin-12; and linomide. (Flier et al., *The New England Journal of Medicine*, vol 333 pp1757–1763, 1995 and the references cited therein)

PKC inhibitors also have been proposed for cancer therapy, see U.S. Pat. No. 5,552,396. However, the effectiveness of the inhibitors of the β isozyme of PKC against particular neoplastic diseases was not known. Given the role VEGF plays in certain neoplastic and other diseases, there is a need in the art to identify additional drugs that are specifically targeted at the function of VEGF.

SUMMARY OF INVENTION

It is an object of the invention to provide a method for treating neoplasia.

It is yet another object of the invention to provide a method for treating rheumatoid arthritis.

It is still yet another object of the invention to provide a method for treating keloid.

It is still another object of the invention to provide a method for treating pulmonary edema associated conditions, such as Adult Respiratory Distress Syndrome (ARDS).

It is still another object of the invention to provide a method for treating carpal tunnel syndrome.

These and other objects of the invention are provided by one or more of the embodiments described below.

In one embodiment of the invention there is provided a method for treating neoplasia which comprises administering to said mammal a therapeutically effective amount of an inhibitor of the β isozyme of protein kinase C.

In yet another embodiment of the invention there is provided a method for treating rheumatoid arthritis which comprises administering to said mammal a therapeutically effective amount of an inhibitor of the P isozyme of protein kinase C.

In another embodiment of the invention there is provided a method for treating keloid which comprises administering to said mammal a therapeutically effective amount of an inhibitor of the β isozyme of protein kinase C.

In yet another embodiment of the invention there is provided a method for treating pulmonary edema which comprises administering to said mammal a therapeutically effective amount of an inhibitor of the β isozyme of protein kinase C.

The present invention provides the art with the identity of compounds which are prophylactic and effective in treating neoplasia, and other disorders associated with vascular endothelial growth factor (VEGF).

BRIEF DESCRIPTION OF THE DRAWINGS

FIG. 1 shows the inhibitory effect of the PKC inhibitor, (S)-3,4-[N,N'-1,1'-((2"-ethoxy)-3'"(O)-4'"-(N,N- dimethylamino)-butane)-bis-(3,3'-indolyl)]-1(H)-pyrrole-2,5-dione on recombinant human VEGF stimulated endothelial cell growth.

Figure 2:
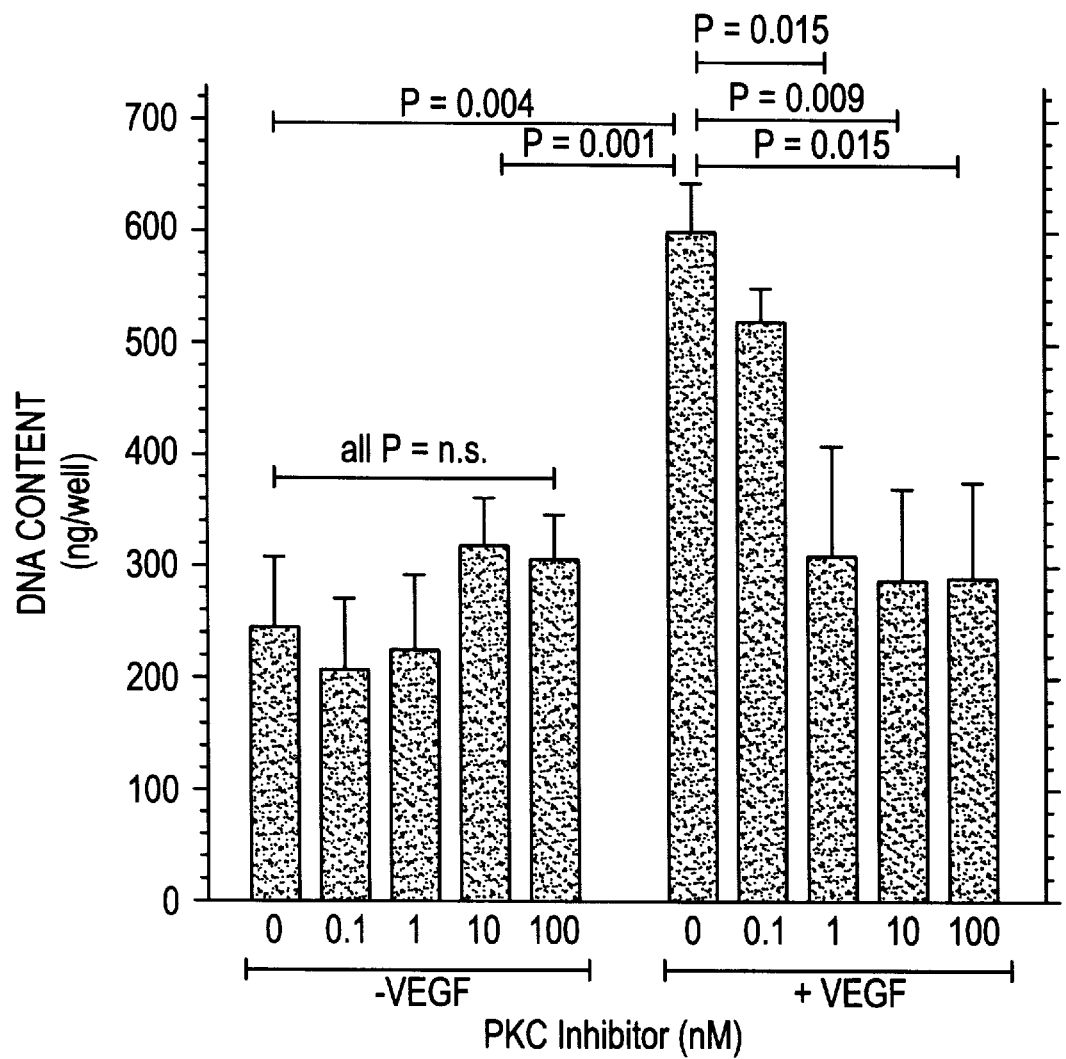

FIG. 2 further illustrates the inhibitory effect of the PKC inhibitor, (S)-3,4-[N,N'-1,1'-((2"-ethoxy)-3'"(O)4'"-(N,N-dimethylamino)-butane)-bis-(3,3'-indolyl)]-1(H)-pyrrole-2,5-dione on recombinant human VEGF stimulated endothelial cell growth.

Figure 3:
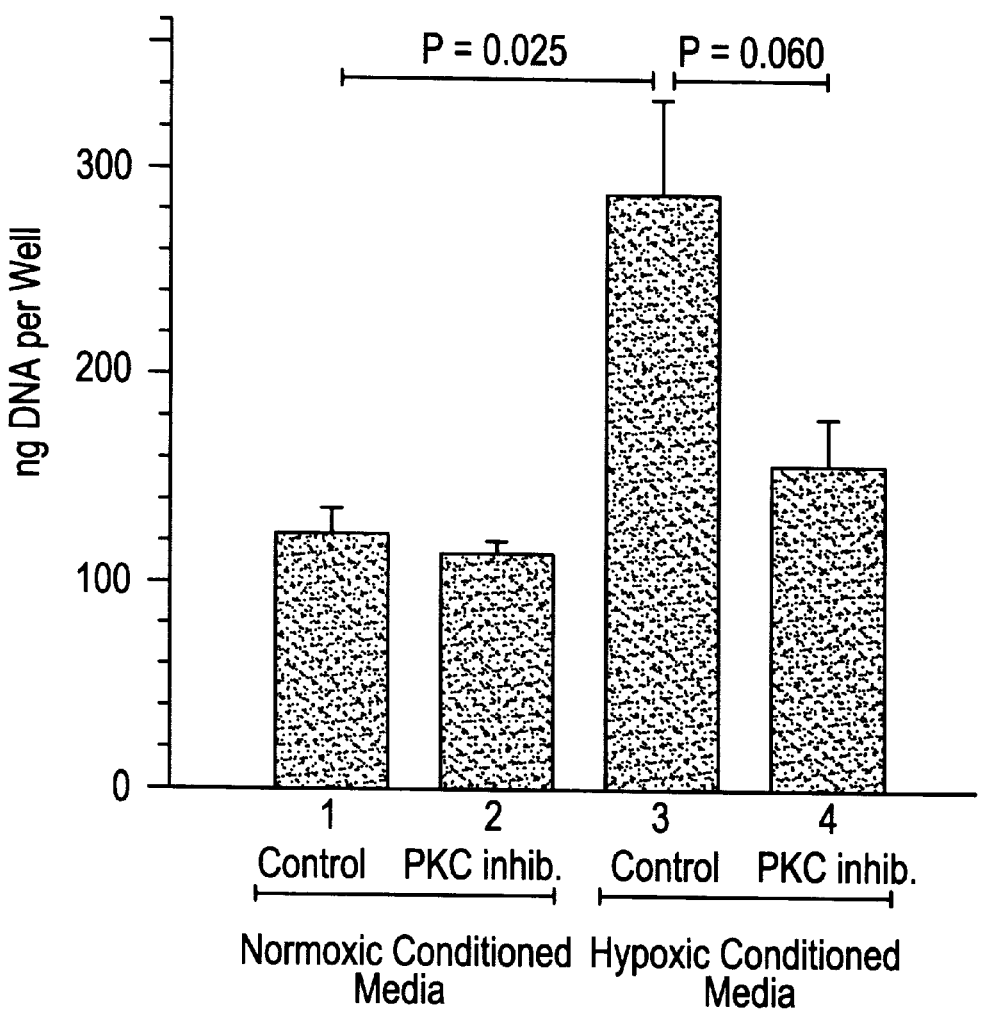

FIG. 3 shows the impact of the PKC inhibitor on the activity of endogenous VEGF expressed upon culturing retinal pericytes under hypoxic conditions.

Figure 4:
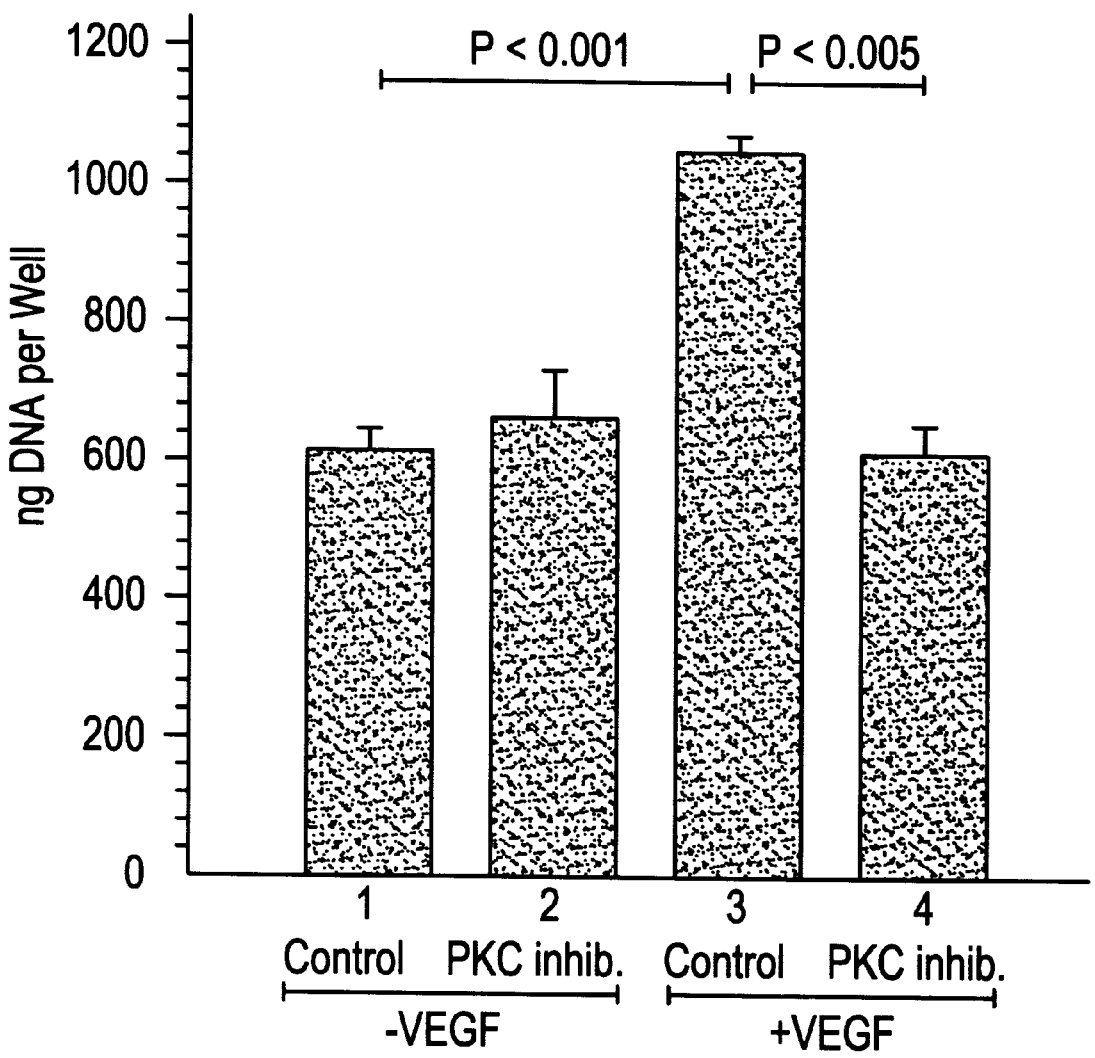

FIG. 4 further illustrate the inhibitory effect of the PKC inhibitor on recombinant human VEGF stimulated endothelial cell growth.

DETAILED DESCRIPTION OF THE INVENTION

It is a discovery of the present invention that the therapeutic use of a particular class of protein kinase C inhibitors, i.e., inhibitors of the β isozyme of protein kinase C, and especially β isozyme selective inhibitors of PKC, counteracts the effects of VEGF. In particular, it is a discovery of the present invention that use of this particular class of protein kinase C inhibitors counteracts endothelial cell growth and capillary permeability, especially the endothelial cell growth and the capillary permeability stimulated by the growth factor VEGF. Consequently, such compounds can be used therapeutically to treat disorders associated with VEGF, such as neoplasia, and other disease conditions that are associated with VEGF.

The method of this invention preferably utilizes those protein kinase C inhibitors that effectively inhibit the β isozyme. One suitable group of compounds are generally described in the prior art as bis-indolylmaleimides or macrocyclic bis-indolylmaleimides. Bis-indolylmaleimides well recognized in the prior art include those compounds described in U.S. Pat. Nos. 5,621,098, 5,552,396, 5,545,636, 5,481,003, 5,491,242, and 5,057,614, all incorporated by reference herein. Macrocyclic bis-indolylmaleimides are particularly represented by the compounds of formula I. These compounds, and methods for their preparation, have been disclosed in U.S. Pat. No. 5,552,396, which is incorporated herein by reference. These compounds are administered in a therapeutically effective amount to a mammal to inhibit endothelial cell growth or capillary permeability associated with VEGF, to inhibit VEGF effects associated with neoplasia, and other disease conditions, e.g., rheumatoid arthritis, keloid, carpal tunnel syndrome and pulmonary edema. These compounds can also be administered to patients at risk of the disease conditions mentioned above as prophylactics.

One preferred class of compounds for use in the method of the invention has the formula:

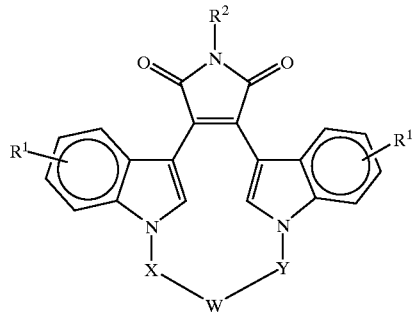

(I)

wherein:
W is —O—, —S—, —SO—, —SO₂—, —CO—, $C_2$–$C_6$ alkylene, substituted alkylene, $C_2$–$C_6$ alkenylene, -aryl-, -aryl($CH_2$)$_m$O—, -heterocycle-, -heterocycle-($CH_2$)$_m$O—, -fused bicyclic-, -fused bicyclic-($CH_2$)$_m$ O—, —$NR^3$—, —$NOR^3$—, —CONH—, or —NHCO—;

X and Y are independently $C_1$–$C_4$ alkylene, substituted alkylene, or together X, Y, and W combine to form —($CH_2$)$_n$—AA—;

$R^1$s are hydrogen or up to four optional substituents independently selected from halo, $C_1$–$C_4$ alkyl, hydroxy, $C_1$–$C_4$ alkoxy, haloalkyl, nitro, $NR^4R^5$, or —NHCO($C_1$–$C_4$ alkyl);

$R^2$ is hydrogen, $CH_3CO$—, $NH_2$, or hydroxy;

$R^3$ is hydrogen, ($CH_2$)$_m$aryl, $C_1$–$C_4$ alkyl, —COO($C_1$–$C_4$ alkyl), —CONR⁴R⁵, —(C═NH)NH₂, —SO($C_1$–$C_4$ alkyl), —SO₂ (NR⁴R⁵), or —SO₂($C_1$–$C_4$ alkyl);

$R^4$ and $R^5$ are independently hydrogen, $C_1$–$C_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5 or a pharmaceutically acceptable salt, prodrug or ester thereof.

A more preferred class of compounds for use in this invention is represented by formula I wherein the moieties —X—W—Y— contain 4 to 8 atoms, which may be substituted or unsubstituted. Most preferably, the moieties —X—W—Y— contain 6 atoms.

Other preferred compounds for use in the method of this invention are those compounds of formula I wherein $R_1$ and $R^2$ are hydrogen; and W is a substituted alkylene, —O—, S—, —CONH—, —NHCO— or —NR3—. Particularly preferred compounds for use in the invention are compounds of the formula Ia:

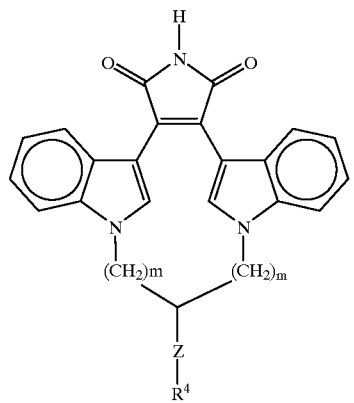

(Ia)

wherein Z is —($CH_2$)$_p$— or —($CH_2$)$_p$—O—($CH_2$)$_p$—; $R^4$ is hydroxy, —SH, $C_1$–$C_4$ alkyl, ($CH_2$)$_m$aryl, —NH(aryl), —N($CH_3$) ($CF_3$), —NH($CF_3$), or —NR⁵R⁶; $R^5$ is hydrogen or $C_1$–$C_4$ alky; $R^6$ is hydrogen, $C_1$–$C_4$ alkyl or benzyl; p is 0, 1, or 2; and m is independently 2 or 3 or a pharmaceutically acceptable salt, prodrug or ester thereof. Most preferred compounds of the formula Ia are those wherein Z is $CH_2$; and $R^4$ is —NH₂, —NH($CF_3$), or —N($CH_3$)₂.

Other preferred compounds for use in the method of the present invention are compounds wherein W in formula I is —O—, Y is a substituted alkylene, and X is an alkylene. These preferred compounds are represented by formula Ib:

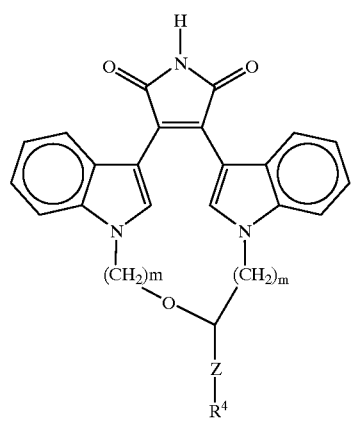

(Ib)

wherein Z is —(CH$_2$)$_p$—; R$^4$ is —NR$^5$R$^6$, —NH(CF$_3$), or —N(CH$_3$)(CF$_3$); R$^5$ and R$^6$ are independently H or C$_1$–C$_4$ alkyl; p is 0, 1, or 2; and m is independently 2 or 3 or a pharmaceutically acceptable salt, prodrug or ester thereof. Most preferred compounds of formula Ib are those wherein p is 1; and R$^5$ and R$^6$ are methyl.

Because they contain a basic moiety, the compounds of formulae I, Ia, and Ib can also exist as pharmaceutically acceptable acid addition salts. Acids commonly employed to form such salts include inorganic acids such as hydrochloric, hydrobromic, hydroiodic, sulfuric and phosphoric acid, as well as organic acids such as para-toluenesulfonic, methanesulfonic, oxalic, para-bromophenylsulfonic, carbonic, succinic, citric, benzoic, acetic acid, and related inorganic and organic acids. Such pharmaceutically acceptable salts thus include sulfate, pyrosulfate, bisulfate, sulfite, bisulfite, phosphate, mono-hydrogenphosphate, dihydrogenphosphate, metaphosphate, pyrophosphate, chloride, bromide, iodide, acetate, propionate, decanoate, caprylate, acrylate, formate, isobutyrate, heptanoate, propiolate, oxalate, malonate, succinate, suberate, sebacate, fumarate, maleate, 2-butyne-1,4-dioate, 3-hexyne-2,5-dioate, benzoate, chlorobenzoate, hydroxybenzoate, methoxybenzoate, phthalate, xylenesulfonate, phenylacetate, phenylpropionate, phenylbutyrate, citrate, lactate, hippurate, β-hydroxybutyrate, glycolate, maleate, tartrate, methanesulfonate, propanesulfonate, naphthalene-1-sulfonate, naphthalene-2-sulfonate, mandelate and the like. Particularly the hydrochloric and mesylate salts are used.

In addition to pharmaceutically-acceptable salts, other salts also can exist. They may serve as intermediates in the purification of the compounds, in the preparation of other salts, or in the identification and characterization of the compounds or intermediates.

The pharmaceutically acceptable salts of compounds of formulae I, Ia, and Ib can also exist as various solvates, such as with water, methanol, ethanol, dimethylformamide, ethyl acetate and the like. Mixtures of such solvates can also be prepared. The source of such solvate can be from the solvent of crystallization, inherent in the solvent of preparation or crystallization, or adventitious to such solvent.

It is recognized that various stereoisomeric forms of the compounds of formulae I, Ia, and Ib may exist; for example, W may contain a chiral carbon atom in the substituted alkylene moiety. The compounds are normally prepared as racemates and can conveniently be used as such. Alternatively, both individual enantiomers can be isolated or synthesized by conventional techniques if so desired. Such racemates and individual enantiomers and mixtures thereof form part of the compounds used in the methods of the present invention.

The compounds utilized in this invention also encompass the pharmaceutically acceptable prodrugs of the compounds of formulae I, Ia, and Ib. A prodrug is a drug which has been chemically modified and may be biologically inactive at its site of action, but which may be degraded or modified by one or more enzymatic or other in vivo processes to the parent bioactive form. This prodrug likely may have a different pharmacokinetic profile than the parent, enabling easier absorption across the mucosal epithelium, better salt formation or solubility, and/or improved systemic stability (an increase in plasma half-life, for example). Typically, such chemical modifications include the following:

1) ester or amide derivatives which may be cleaved by esterases or lipases;
2) peptides which may be recognized by specific or nonspecific proteases; or
3) derivatives that accumulate at a site of action through membrane selection of a prodrug form or a modified prodrug form; or any combination of 1 to 3, supra. Conventional procedures for the selection and preparation of suitable prodrug derivatives are described, for example, in H. Bundgaard, *Design of Prodrugs*, (1985).

The synthesis of various bis-indole-N-maleimide derivatives is described in Davis et al. U.S. Pat. No. 5,057,614 and the synthesis of the preferred compounds suitable for use in this invention are described in the previously identified U.S. Pat. No. 5,552,396 and in Faul et al. EP publication 0 657 411 A1, all of which are incorporated herein by reference.

One particularly preferred protein kinase C inhibitor for use in the method of this invention is the compound described in Example 5 g ((S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione Hydrochloride Salt) of the aforementioned U.S. Pat. No. 5,552,396. This compound is a potent protein kinase C inhibitor. It is selective to protein kinase C over other kinases and is highly isozyme-selective, i.e., it is selective for the beta-1 and beta-2 isozymes. Other salts of this compound also would be favored, especially the mesylate salts.

A preferred mesylate salt can be prepared by reacting a compound of the formula II:

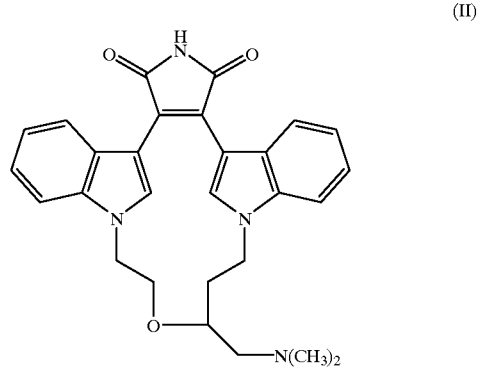

(II)

with methanesulfonic acid in a non-reactive organic solvent, preferably an organic/water mixture, and most preferably water-acetone. Other solvents such as methanol, acetone, ethylacetate and mixtures thereof are operable. The ratio of solvent to water is not critical and generally determined by the solubility of the reagents. Preferred solvent to water ratios are generally from 0.1:1 to 100:1 solvent to water by volume. Preferably, the ratio is 1:1 to 20:1 and most preferably 5:1 to 10:1. The optimal ratio is dependent on the solvent selected and is preferably acetone at a 9:1 solvent to water ratio.

The reaction usually involves approximately equimolar amounts of the two reagents, although other ratios, especially those wherein the methanesulfonic acid is in excess, are operative. The rate of addition of methanesulfonic acid is not critical to the reaction and may be added rapidly (<5 minutes) or slowly over 6 or more hours. The reaction is carried out at temperatures ranging from 0° C. to reflux. The reaction mixture is stirred until formation of the salt is complete, as determined by x-ray powder diffraction and can take from 5 minutes to 12 hours.

The salts of the present invention are preferably and readily prepared as a crystalline form. The trihydrate form of the salt may be readily converted to the monohydrate upon drying or exposure to 20–60% relative humidity. The salt is substantially crystalline demonstrating a defined melting point, birefringence, and an x-ray diffraction pattern. Generally, the crystals have less than 10% amorphous solid and preferably less than 5% and most preferably less than 1% amorphous solid.

The mesylate salt is isolated by filtration or other separation techniques appreciated in the art directly from the reaction mixture in yields ranging from 50% to 100%. Recrystallization and other purification techniques known in the art may be used to purify the salt further if desired.

Endothelial cells in tissue culture stimulated by growth factors such as VEGF exhibit a greater growth rate than the basal cellular growth rate. Experiments performed in the present invention have shown that when administered in vitro, at a concentration of about 0.1 to 100 nM, the protein kinase C inhibitor, (S)-3,4-[N,N'-1,1'-((2"-ethoxy)-3'''(O)-4'''-(N,N-dimethylamino)-butane)-bis-(3,3'-indolyl)]-1(H)-pyrrole-2,5-dione acid salt, significantly inhibits growth factor (such as VEGF) stimulated non-basal cell growth.

Importantly, other testings have demonstrated that normal endothelial cell growth in tissue culture is not inhibited by this compound, as shown by the lack of inhibition of endothelial cell growth without VEGF stimulation in normoxic conditional media. In hypoxic conditioned media, the cell growth rate increases due to the increase in the content of endogenous growth factor, VEGF, produced by the hypoxic cells. Again, the P-isozyme selective protein kinase C inhibitor (S)-3,4-[N,N'-1,1'-((2"-ethoxy)-3'''(O)-4'''-(N,N-dimethylamino)-butane)-bis-(3,3'-indolyl)]-1(H)-pyrrole-2,5-dione acid salt normalizes the cell growth induced by such hypoxic conditions.

Experiments provided in the present invention demonstrate that capillary permeability is also affected by growth factors such as VEGF. Testing has shown that in an animal model, VEGF significantly increases the capillary permeability up to 3 fold. This VEGF dependent capillary permeability increase is also dose dependent. According to the in vivo animal testing, administrating protein kinase C inhibitor at a concentration of about 25 mg/kg/day prior to VEGF challenge greatly inhibited the capillary permeability induced by VEGF. Use of concentrations from 1 nM to 5 mM, and preferably from 1 nM to 500 nM are specifically contemplated. The inhibition can be up to 80% and is generally specific to growth factor induced capillary permeability. Capillary permeability can be measured by fluorescein angiography.

The PKC-β inhibitors of the present invention can be used to treat the disease conditions associated with endothelial cell growth and capillary permeability, especially neoplasia, and other VEGF related diseases.

Pulmonary edema is also treatable by the compounds of the present invention. Pulmonary edema is characterized by increases in the interstitial liquid content of the lungs due to increased capillary permeability. Pulmonary edema can be associated with several disease conditions including Adult Respiratory Distress Syndrome (ARDS). It is likely to be associated primarily with disruption of the alveolar-capillary membranes which could induce hypoxia and subsequent increase in VEGF content. Such disruption could also activate PKC β. Therefore, the compounds identified in the present invention can interfere with the stimulation of capillary permeability by growth factors and/or PKC β and ameliorate the conditions that lead to pulmonary edema.

The PKC inhibitors of the present invention can also be used to treat neoplasia and other VEGF related diseases in a mammal. The signal transduction pathway of VEGF has direct effects on tumor cells as well as mediates the angiogenic activities in a wide range of neoplastic and non-neoplastic disease conditions. VEGF expression has been demonstrated in a variety of human tumors such as capillary hemangioblastomia, breast cancer, Kaposi's sarcoma, glioblastoma, angiomatous disorders, colorectal cancer, medulloblastoma, gastric carcinoma, adenocarcinomas of the gastrointerestinal tract, malignant melanoma, ovarian cancer, non small cell lung cancer, prostate cancer, bladder carcinoma, von Hippel Lindau Syndrome, renal cell carcinoma, skin cancer, thyroid malignancies, cervical cancer, hepatocellular carcinoma, rhabdomyosarcoma, and leiomysarcoma.

The poor prognosis of a tumor is often associated with the degree of tumor vascularity coupled with VEGF expression. Without a vascular supply, tumor growth is limited. Therefore use of an antiangiogenic agent or anti-VEGF agent may prevent further growth and induce regression of tumors by limiting vascular supply. Anti-VEGF agents may also have direct effects on tumor cells, e.g., VEGF directly affects malignant melanoma cells.

The expression of VEGF is controlled by multiple mechanisms. VEGF production can be positively modulated by hypoxia, certain oncgenea and various cytokines factor including transforming growth factor-beta (TGF-β) and platelet derived growth In a preferred embodiment, PKC-β inhibitors can be used in anti-VEGF therapy to treat a human with neoplasia. Any neoplastic growth expressing VEGF, e.g., the tumors listed above, can be affected by the PKC-β inhibitors of the present invention. The anti-VEGF therapy is especially preferred to treat a human with unresectable primary tumors, primary tumors that are incompletely removed by surgical or radiotherapeutic techniques, primary tumors which have been adequately treated but who are at high risk to subsequently develop metastatic disease, and those with an established metastatic disease. Groups of tumors having a worse prognosis conferred by a high degree of vascularity e.g., breast cancer, prostate cancer, colon cancer, melanoma cancer, non small cell lung cancer and head/neck carcinoma are especially good candidates for the anti-VEGF therapy or PKC-β inhibitor treatment of the invention.

Hemangioma of infancy occurs in 10–12% of white infants. Generally, it is not a life threatening disorder but in some cases either due to size or anatomic location can cause significant morbidity and mortality. VEGF has been implicated in the growth of these tumors. Currently, interferon α-2a is utilized to induce regression of this tumor. Given the angiogenic nature of this tumor, anti-VEGF therapy employing PKC-β inhibitors should be as efficacious as interferon α-2a or could be assessed as salvage therapy for use upon interferon α-2a failure.

PKC-β inhibitors or anti-VEGF therapy could also be used to treat tumor induced ascites, malignant pleural effusions and peritumoral edema. Given that VEGF is increased in the acitic fluid of females having ovarian hyperstimulation syndrome post induction of ovulation, a PKC-β inhibitor could be of use in this condition. VEGF is a vascular permeability factor with a high potency, e.g., 50,000 fold greater than histamine. VEGF concentration is elevated in fluid removed from patients with pleural and peritoneal effusions due to malignancy. Intraperitoneal injection of tumor cells into nude mice results in accumulation of ascites that temporally correlates with increasing secretion of VEGF into peritoneum. Peritumoral edema occurring in central nerve system neoplasms such as glioblastoma is associated with high level of VEGF. Anti-VEGF therapy will reduce ascites and pleural effusions associated with malignancy and ovarian hyperstimulation syndrome. Such therapy will decrease the need for repeated paracentesis/thoracentesis and the attendant morbidity associated with these procedures e.g., infection, protein depletion, collapsed lung, etc. Such therapy is especially preferred for inhibition of peritumorial edema occurring in closed anatomic areas, such as central nerve system.

The PKC-β inhibitors used in the present invention can also be used in anti-VEGF therapies to treat other diseases associated with VEGF expression.

Rheumatoid arthritis is characterized by a hyperplastic synovial pannus with a high degree of vascularity which invades and destroys the normal joint architecture. In addition, the exudative nature of synovial fluid suggests a heightened degree of capillary permeability. VEGF can stimulate collagenase expression and further worsen the destructive process. VEGF levels are significantly elevated in synovial fluid derived from patients with rheumatoid arthritis as compared to patients with osteoarthritis. VEGF production has also been localized to infiltrating macrophages. Therefore, rheumatoid arthritis could be treated by administering PKC-β inhibitors in anti-VEGF therapy.

Keloid is characterized by exuberant granulation tissue formation during wound healing that results in hypertrophic scarring. This disorder is typically seen in black patients and tends to be a recurrent disorder. Topical application of PKC inhibitors to hypertrophic granulation tissue could reduce angiogenesis and lessen subsequent scar formation.

Carpal tunnel syndrome, also called entrapment neuropathy, is characterized by compression of nerves which can lead to sensory alternations, muscle weakness, and muscle wasting. It is caused by pressure on the median nerve as it passes through the space formed by the bones of the wrist and the transverse carpal ligament. Carpal tunnel syndrome occurs either as a diabetes related syndrome or in non-diabetic populations.

The enhanced nerve hydration in carpal tunnel syndrome can be caused by elevated level of VEGF. Increased VEGF levels in the nerve surrounding tissues could cause nerve entrapment by inducing vascular permeability and fluid efflux into the perineural tissues. Alteration of synthesis and/or degradation of collagen in carpal tunnel syndrome can be caused by high level of TGF-β production. The increased TGF-β expression could enhance the extracellular protein synthesis including collagen and reduce the degradation thereof which leads to an increased extracellular matrix deposition in the nerve surrounding tissues. PKC activation has been shown to induce the transcription of TGF-β by stimulating activator protein-1 activity. Therefore, PKC-β inhibitors of the present invention can be used to counteract VEGF and/or TGF-β activity in carpal tunnel syndrome.

One skilled in the art will recognize that a therapeutically effective amount of the protein kinase C-β inhibitors used in accordance with the present invention is the amount sufficient to inhibit the growth of endothelial cells or development of capillary permeability by inhibiting VEGF and that this amount varies inter alia, depending upon an affected tissue size, the concentration of the compound in the therapeutic formulation, and the body weight of the patient. Generally, an amount of protein kinase C inhibitor to be administered as a therapeutic agent for treating neoplasia and other VEGF related diseases discussed above will be determined on a case by case basis by the attending physician. As a guideline, the extent of the neovascularization, the body weight and age of the patient will be considered when setting an appropriate dose.

Generally, a suitable dose is one that results is a concentration of the protein kinase C inhibitor at the treatment site in the range of 0.5 nM to 200 μM, and more usually 0.5 nM to 200 nM. It is expected that serum concentrations of 0.5 nM to 100 nM should be sufficient in most circumstances.

To obtain these treatment concentrations, a patient in need of treatment likely will be administered between about 0.001 mg per day per kg of body weight and 50.0 mg per day per kg. Usually, not more than about 1.0 to 10.0 mg per day per kg of body weight of protein kinase C-β inhibitor should be needed. As noted above, the above amounts may vary on a case-by-case basis.

The compounds of formula I and the preferred compounds of formula Ia and Ib are preferably formulated prior to administration. Suitable pharmaceutical formulations are prepared by known procedures using well known and readily available ingredients. In making the compositions suitable for use in the method of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), soft and hard gelatin capsules, suppositories, sterile injectable solutions and sterile packaged powders for either oral or topical application.

Some examples of suitable carriers, excipient, and diluents include lactose, dextrose, sucrose sorbitol, mannitol, starches, gum acacia, calcium phosphates, alginate, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient. The compositions are preferably formulated in a unit dosage form, each dosage containing from about 0.05 mg to about 3 g, more usually about 750 mg of the active ingredient.

However, it will be understood that the therapeutic dosage administered will be determined by the physician in the light of the relevant circumstances including the severity of the condition to be treated, the choice of compound to be administered and the chosen route of administration. Therefore, the above dosage ranges are not intended to limit the scope of the invention in any way. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

In addition to the above formulations, most of which may be administered orally, the compounds used in the method of the present invention also may be administered topically. Topical formulations include ointments, creams and gels.

Ointments generally are prepared using either (1) an oleaginous base, i.e., one consisting of fixed oils or hydrocarbons, such as white petrolatum or mineral oil, or (2) an absorbent base, i.e., one consisting of an anhydrous substance or substances which can absorb water, for example anhydrous lanolin. Customarily, following formation of the base, whether oleaginous or absorbent, the active ingredient (compound) is added to an amount affording the desired concentration.

Creams are oil/water emulsions. They consist of an oil phase (internal phase), comprising typically fixed oils, hydrocarbons, and the like, such as waxes, petrolatum, mineral oil, and the like, and an aqueous phase (continuous phase), comprising water and any water-soluble substances, such as added salts. The two phases are stabilized by use of an emulsifying agent, for example, a surface active agent, such as sodium lauryl sulfate; hydrophilic colloids, such as acacia colloidal clays, veegum, and the like. Upon formation of the emulsion, the active ingredient (compound) customarily is added in an amount to achieve the desired concentration.

Gels comprise a base selected from an oleaginous base, water, or an emulsion-suspension base. To the base is added a gelling agent which forms a matrix in the base, increasing its viscosity. Examples of gelling agents are hydroxypropyl cellulose, acrylic acid polymers, and the like. Customarily, the active ingredient (compounds) is added to the formulation at the desired concentration at a point preceding addition of the gelling agent.

The amount of compound incorporated into a topical formulation is not critical; the concentration should be within a range sufficient to permit ready application of the formulation to the affected tissue area in an amount which will deliver the desired amount of compound to the desired treatment site.

The customary amount of a topical formulation to be applied to an affected tissue will depend upon an affected tissue size and concentration of compound in the formulation. Generally, the formulation will be applied to the effected tissue in an amount affording from about 1 to about 500 μg compound per cm$^2$ of an affected tissue. Preferably, the applied amount of compound will range from about 30 to about 300 μg/cm$^2$, more preferably, from about 50 to about 200 μg/cm$^2$, and, most preferably, from about 60 to about 100 μg/cm$^2$.

The following formulation examples are illustrative only and are not intended to limit the scope of the invention in any way.

Formulation 1

Hard gelatin capsules are prepared using the following ingredients:

|  | Quantity (mg/capsule) |
| --- | --- |
| Active agent | 250 |
| starch, dried | 200 |
| magnesium stearate | 10 |
| Total | 460 mg |

The above ingredients are mixed and filled into hard gelatin capsules in 460 mg quantities.

Formulation 2

A tablet is prepared using the ingredients below:

|  | Quantity (mg/capsule) |
| --- | --- |
| Active agent | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

Formulation 3

Tablets each containing 60 mg of active ingredient are made as follows:

|  | Quantity (mg/tablet) |
| --- | --- |
| Active agent | 60 mg |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLES

These examples all demonstrate the use of (S)-3,4-[N,N'-1,1'-((2"-ethoxy)-3'''(O)-4'''-(N,N-dimethylamino)-butane)-bis-(3,3'-indolyl)]-1(H)-pyrrole-2,5-dione hydrochloride salt to inhibit in vitro endothelial cell growth and in vivo increased capillary permeability stimulated by VEGF.

Example 1

In this example, the inhibitory effect of the noted compound on VEGF stimulated endothelial cell growth was examined using recombinant human VEGF.

Bovine retinal endothelial cells were isolated from fresh calf eyes by homogenization and a series of filtration steps. Primary endothelial cell cultures were grown in fibronectin (NYBen Reagents, New York Blood Center)-coated dishes (Costar) containing Dulbecco's modified Eagle's medium (DMEM) with 5.5 mM glucose, 10% plasma-derived horse serum (Wheaton, Scientific). 50 mg of heparin per liter and 50 units of endothelial cell growth factor per liter (Boehringer Mannheim). After the cells reached confluence, the medium was changed to include 5% fetal bovine serum (HyClone). Medium was changed every 3 days. Endothelial cell homogeneity was confirmed with anti-factor VIII antibodies.

The effect of the noted PKC inhibitor on VEGF action in vitro was evaluated by using sparsely plated cultures of the bovine retinal microvascular endothelial cells, which undergo growth stimulation upon addition of VEGF. Bovine retinal endothelial cells were plated sparsely (~2500 cells per well) in 24-well dishes (Costar), incubated overnight in DMEM containing 10% calf serum (GIBCO). The medium was changed the next day.

To examine the impact of the noted PKC inhibitor on endothelial cell growth, one set of experiments was conducted in which the cell growth in the absence of any active agent served as a control, and then the impact of the addition of the noted PKC inhibitor in both the presence of VEGF (25 ng/ml; Genentech) and in the absence of VEGF was examined. After incubation at 37° C. for 4 days, the cells were lysed in 0.1% sodium dodecyl sulfate (SDS) and DNA content was measured using Hoechst 33258 dye and a fluorometer (model TKO-100; Hoefer).

All determinations were performed at least in triplicate and experiments were repeated a minimum of three times. Results are expressed as means±SD for all experiments. Analysis of in vitro results was performed by non-paired Student's t test. A P value of<0.050 was considered statistically significant.

Figure 1:
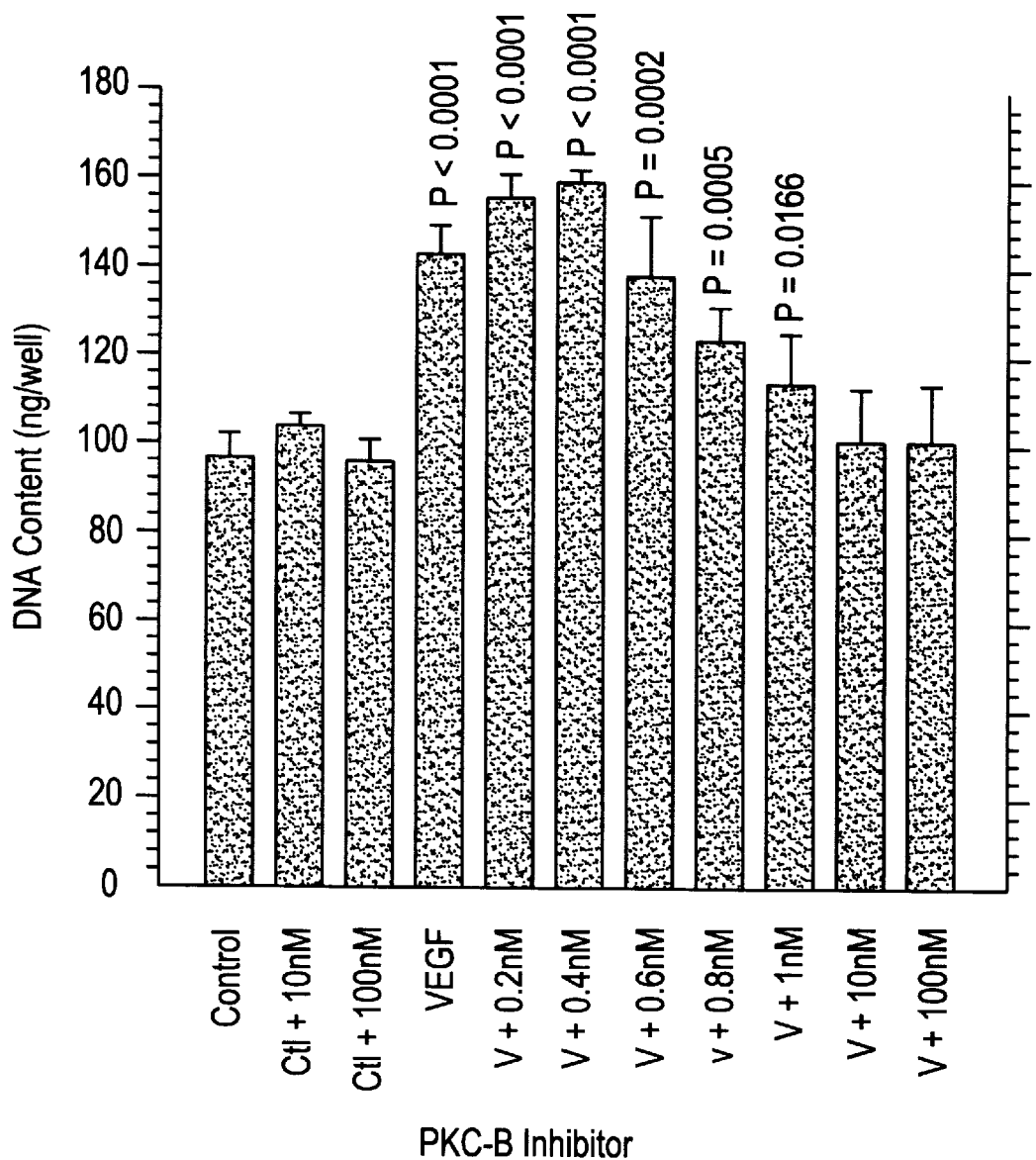

FIG. 1 illustrates the results obtained using recombinant VEGF. As shown by the three left-most columns of the figure, the addition of the noted PKC inhibitor to the endothelial cell culture had essentially no impact on the basal growth rate (column one). The growth rate increased substantially upon the addition of VEGF (fourth column). This growth rate was curtailed significantly upon the addition of>0.5nM of the noted PKC inhibitor (four right-most columns).

Example 2

This example is similar to the work reported in FIG. 1 and further illustrates the inhibitory effect of the noted PKC inhibitor on VEGF stimulated endothelial cell growth using recombinant human VEGF.

Using the procedures of Example 1, bovine retinal endothelial cells were isolated and grown; then sparsely plated cultures were prepared. Again, using the procedure of Example 1, experiments were conducted in which the affect of the noted PKC inhibitor on endothelial cell growth in both the presence of VEGF (25 ng/ml; Genentech) and in the absence of VEGF was examined. After incubation at 37° C. for 4 days, the cells were lysed in 0.1% sodium dodecyl sulfate (SDS) and DNA content was measured using Hoechst 33258 dye and a fluorometer (model TKO-100; Hoefer).

FIG. 2 illustrates the results of this work. As shown by the columns above the legend−VEGF, the addition of the noted PKC inhibitor to the endothelial cell culture at from 0.1 nM to 100 nNM had essentially no impact on the basal growth rate of the cells. Stimulation of the endothelial cells with recombinant human VEGF (25 ng/ml) produced a significant increase in cellular DNA content after 4 days, indicative of an increase in growth rate, compared with unstimulated cells (compare−VEGF at 0 with+VEGF at 0). This growth rate was curtailed significantly upon the addition of the noted PKC inhibitor (four right-most columns above legend+VEGF). In particular, the VEGF stimulatory capac-ity was reduced slightly in the presence of 0.1 nM of the PKC inhibitor and was essentially entirely eliminated by simultaneous addition of 1 nM and greater of the PKC inhibitor.

Example 3

This example examines the impact of the noted PKC inhibitor on the activity of endogenous VEGF expressed upon culturing retinal pericytes under hypoxic conditions.

Bovine retinal endothelial cells and retinal pericytes were isolated from fresh calf eyes by homogenization and a series of filtration steps. The endothelial cells were grown and sparsely cultured on plates using the procedures of Example 1. Using similar techniques, bovine retinal pericytes were cultured in DMEM/5.5 mM glucose with 20% fetal bovine serum.

Hypoxic conditioned medium for endogenous VEGF expression and normoxic conditioned control medium were prepared respectively according to the following procedures. Confluent retinal pericyte monolayers were exposed for 24 hr to 2% $O_2$/5% $CO_2$/93% $N_2$ using a Lab-Line Instruments advanced computer controlled infrared water-jacketed $CO_2$ incubator with reduced oxygen control (model 480). All cells were maintained at 37° C. and showed no morphologic changes by light microscopy, excluded trypan blue dye (>98%) and could subsequently be passaged normally. Cells incubated under normoxic conditions (95% air/5% $CO_2$) from the same batch and passage were used as controls. Medium was subsequently collected and filtered (Nalgene; 0.22 μm) prior to use.

In this example, experiments were conducted in which the affect of the noted PKC inhibitor on endothelial cell growth in the presence of either normoxic conditioned media or hypoxic conditioned media was examined. As was done in the previous examples, after incubation at 37° C. for 4 days, the cells were lysed in 0.1% sodium dodecyl sulfate (SDS) and DNA content was measured using Hoechst 33258 dye and a fluorometer (model TKO-100; Hoefer).

In the tests reported in FIG. 3, the noted PKC inhibitor was used at a concentration of 10 nM. As shown in FIG. 3, retinal endothelial cell growth was stimulated by conditioned medium from retinal pericytes cultured under hypoxic conditions known to induce VEGF expression (compare column 1 to column 3 in FIG. 3). This growth stimulation was suppressed (normalized) in the presence of the hydrochloric acid salt of (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione of the PKC inhibitor (compare 3 to column 4).

Example 4

This example is similar to the work reported in FIGS. 1 and 2 and further illustrates the inhibitory effect of the noted PKC inhibitor on VEGF stimulated endothelial cell growth using recombinant human VEGF.

Using the procedures of Example 1, bovine retinal endothelial cells were isolated and grown; then sparsely plated cultures were prepared. Again, using the procedure of Example 1, experiments were conducted in which the affect of the noted PKC inhibitor on endothelial cell growth in both the presence (+VEGF)(25 ng/ml; Genentech) and absence of VEGF (−VEGF) were examined. As above, after incubation at 37° C. for 4 days, the cells were lysed in 0.1% sodium dodecyl sulfate (SDS) and DNA content was measured using Hoechst 33258 dye and a fluorometer (model TKO-100; Hoefer).

FIG. 4 illustrates the results of this work. As shown by the columns above the legend–VEGF, the addition of the noted PKC inhibitor to the endothelial cell culture at a concentration of 10 nM had essentially no impact on the basal growth rate of the cells. Stimulation of the endothelial cells with recombinant human VEGF (25 ng/ml) produced a significant increase in cellular DNA content, indicative of an increase in growth rate, compared with unstimulated cells (compare–VEGF Control with+VEGF Control). This growth rate was curtailed significantly upon the addition of the noted PKC inhibitor at a concentration of 10 nM.

These results demonstrate that the disclosed class of PKC inhibitors and particularly, (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione, prevents in vitro stimulation of retinal endothelial cell growth by both exogenous and hypoxia-induced VEGF. Since VEGF expression has been linked closely with neovascularization associated with macular degeneration, these results support the use of these PKC inhibitors as a therapy for the treatment of macular degeneration.

The principles, preferred embodiments and modes of operation of the present invention have been described in the foregoing specification. The invention which is intended to be protected herein, however, is not to be construed as limited to the particular forms disclosed, since they are to be regarded as illustrative rather than restrictive. Variations and changes may be made by those skilled in the art without departing from the spirit of the invention.

What is claimed is:

1. A method for treating Carpal tunnel syndrome, which comprises administering to a mammal in need of such treatment, a therapeutically effective amount of an inhibitor of the β isozyme of protein kinase C of the following formula

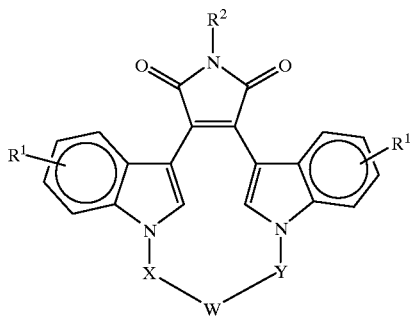

(I)

wherein:

W is —O—, —S—, —SO—, —SO$_2$—, —CO—, $C_2$-$C_6$ alkylene, substituted alkylene, $C_2$-$C_6$ alkenylene, -aryl-, -aryl(CH$_2$)$_m$O—, -heterocycle-, -heterocycle-(CH$_2$)$_m$O—, -fused bicyclic-, -fused bicyclic-(CH$_2$)$_m$O—, —NR$^3$—, —NOR$^3$—, —CONH—, or —NHCO—;

X and Y are independently $C_1$-$C_4$ alkylene, substituted alkylene, or together X, Y, and W combine to form —(CH$_2$)$_n$—AA—;

R$^1$s are hydrogen or up to four optional substituents independently selected from halo, $C_1$-$C_4$ alkyl, hydroxy, $C_1$-$C_4$ alkoxy, haloalkyl, nitro, NR$^4$R$^5$, or —NHCO($C_1$-$C_4$ alkyl);

R$^2$ is hydrogen, CH$_3$CO—, NH$_2$, or hydroxy;

R$^3$ is hydrogen, (CH$_2$)$_m$aryl, $C_1$-$C_4$ alkyl, —COO($C_1$-$C_4$ alkyl), —CONR$^4$R$^5$, —(C=NH)NH$_2$, —SO($C_1$-$C_4$ alkyl), —SO$_2$(NR$^4$R$^5$), or —SO$_2$($C_1$-$C_4$ alkyl);

R$^4$ and R$^5$ are independently hydrogen, $C_1$-$C_4$ alkyl, phenyl, benzyl, or combine to the nitrogen to which they are bonded to form a saturated or unsaturated 5 or 6 member ring;

AA is an amino acid residue;

m is independently 0, 1, 2, or 3; and n is independently 2, 3, 4, or 5, or a pharmaceutically acceptable salt or ester thereof.

2. The method of claim 1 wherein the protein kinase C inhibitor has the following formula:

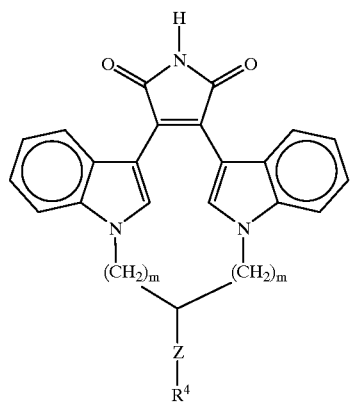

(Ia)

wherein Z is —(CH$_2$)p— or —(CH$_2$)p—O—(CH$_2$)p; R$^4$ is hydroxy, —SH, $C_1$-$C_4$ alkyl, (CH$_2$)$_m$aryl, —NH(aryl), —N(CH$_3$)(CF$_3$), —NH(CF$_3$), or —NR$^5$R$^6$; R$^5$ is hydrogen or $C_1$-$C_4$ alky; R$^6$ is hydrogen, $C_1$-$C_4$ alkyl or benzyl; p is 0, 1, or 2; and m is independently 2 or 3, or a pharmaceutically acceptable salt or ester thereof.

3. The method of claim 1 wherein the protein kinase C inhibitor has the following formula:

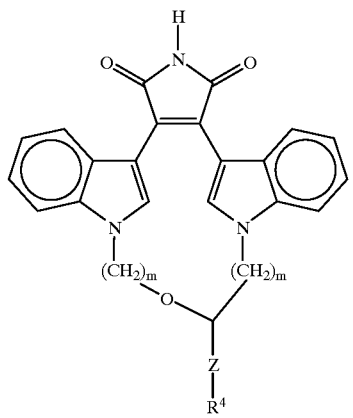

(Ib)

wherein Z is —(CH$_2$)p—; R$^4$ is —NR$^5$R$^6$, —NH(CF$_3$) or —N(CH$_3$) (CF$_3$); R and R$^6$ are independently H or $C_1$-$C_4$alkyl; p is 0, 1, or 2; and m is independently 2 or 3, or a pharmaceutically acceptable salt or ester thereof.

4. The method of claim 1, wherein the protein kinase C inhibitor comprises (S)-3,4-[N,N'-1,1'-((2"-ethoxy)-3'"(O)-4'"-(N,N-dimethylamino)-butane)-bis-(3,3'-indolyl)]-1(H)-pyrrole-2,5-dione or its pharmaceutically acceptable acid salt.

* * * * *